(12) United States Patent
Hirsch (10) Patent No.: US 9,107,985 B2
(45) Date of Patent: Aug. 18, 2015

(54) WOUND TREATMENT CONTAINMENT APPARATUS (75) Inventor: Elliot M. Hirsch, Chicago, IL (US)

(73) Assignee: NORTHWESTERN UNIVERSITY, Evanston, IL (US)

(*) Notice: Subject to any disclaimer, the term of this patent is extended or adjusted under 35 U.S.C. 154(b) by 675 days.

(21) Appl. No.: 13/223,453

(22) Filed: Sep. 1, 2011

(65) Prior Publication Data
US 2012/0010578 A1 Jan. 12, 2012

Related U.S. Application Data (63) Continuation-in-part of application No. 12/608,617, filed on Oct. 29, 2009, now Pat. No. 8,636,709.

(60) Provisional application No. 61/379,058, filed on Sep. 1, 2010, provisional application No. 61/109,360, filed on Oct. 29, 2008.

(51) Int. Cl.
A61M 27/00 (2006.01)
A61M 1/00 (2006.01)

(52) U.S. Cl.
CPC ........... A61M 1/0058 (2013.01); A61M 1/0088 (2013.01); A61M 27/002 (2013.01)

(58) Field of Classification Search
CPC ........... A61M 1/00; A61M 27/00; A61F 5/44; A61B 5/20
USPC .................. 604/289, 290, 304, 305, 313, 319
See application file for complete search history.

(56) References Cited

U.S. PATENT DOCUMENTS

| 6,458,109 | B1 * | 10/2002 | Henley et al. | 604/304 |
| 7,485,112 | B2 * | 2/2009 | Karpowicz et al. | 604/304 |
| 2001/0031943 | A1 * | 10/2001 | Urie | 604/43 |
| 2005/0113742 | A1 | 5/2005 | Yoo | |
| 2006/0253089 | A1 | 11/2006 | Lin | |
| 2007/0225663 | A1 | 9/2007 | Watt et al. | |
| 2008/0306456 | A1 * | 12/2008 | Riesinger | 604/316 |
| 2010/0324510 | A1 * | 12/2010 | Andresen et al. | 604/319 |

FOREIGN PATENT DOCUMENTS

WO 2008/112304 9/2009

OTHER PUBLICATIONS

Davies, "Synthetic materials for covering burn wounds: progress towards perfection. Part I. Short term dressing materials," Burns, 10:94-103, 1983.

(Continued)

Primary Examiner — Melanie Hand
(74) Attorney, Agent, or Firm — Casimir Jones S.C.

(57) ABSTRACT

The invention relates to the treatment of wounds. In particular, the invention relates to systems, devices, and methods enabling treatment (e.g., debridement) of wounds with liquid, gas, or particles in a non-controlled setting while providing containment of contaminated liquid, gas or particles, thereby preventing exposure of individuals and surfaces in proximity to the patient to infectious materials. In certain embodiments, the systems and devices are conformable to the contours of a non-planar surface, such as the human body (e.g., to seal or partially seal the device or system to a portion of a human body).

19 Claims, 8 Drawing Sheets (56) References Cited

OTHER PUBLICATIONS

Granick et al., "Comparison of wound irrigation and tangential hydrodissection in bacterial clearance of contaminated wounds: results of a randomized, controlled clinical study," Ostomy Wound Manage, 53: 64-66, 68-70, 72, 2007.

Kannon et al., "Moist wound healing with occlusive dressings. A clinical review," Dermatol Surg, 21: 583-590, 1995.

Rodeheaver et al. "Wound Cleansing, Wound Irrigation, Wound Disinfection," Chronic Wound Care: A Clinical Source Book For Healthcare Professionals, 4th ed, Alvern PA, Krasner et al. eds., HMP Communications, 331-342, 2007.

Maragakis et al., "An outbreak of multidrug-resistant *Acinetobacter baumannii* associated with pulsatile lavage wound treatment," JAMA, 292: 3006-3011, 2004.

Svoboda et al., "Comparison of bulb syringe and pulsed lavage irrigation with use of a bioluminescent musculoskeletal wound model," J Bone Joint Surg Am, 88:2167-2174, 2006.

\* cited by examiner

ND TREATMENT CONTAINMENT APPARATUS

CROSS-REFERENCE TO RELATED APPLICATIONS

The present invention claims priority to U.S. Provisional Patent Application Ser. No. 61/379,058, filed Sep. 1, 2010, which is herein incorporated by reference in its entirety. The present application is also a Continuation-in-part of U.S. application Ser. No. 12/608,617 filed Oct. 29, 2009, which claims priority to U.S. Provisional Application 61/109,360, filed Oct. 29, 2008, both of which are herein incorporated by reference in their entireties.

FIELD OF INVENTION

The invention relates to the treatment of wounds. In particular, the invention relates to systems, devices, and methods enabling treatment (e.g., debridement) of wounds with liquid, gas, or particles in a non-controlled setting while providing containment of contaminated liquid, gas or particles, thereby preventing exposure of individuals and surfaces in proximity to the patient to infectious materials. In certain embodiments, the systems and devices are conformable to the contours of a non-planar surface, such as the human body (e.g., to seal or partially seal the device or system to a portion of a human body).

BACKGROUND

Chronic wounds have an enormous impact on the US population. Between 1.3-3 million US individuals suffer from pressure ulcers (Kuehn (2007) *JAMA* 297:938-9; herein incorporated by reference). Of the 20 million Americans with diabetes, approximately 10-20% are at risk for developing diabetic ulcers (Kuehn (2007) *JAMA* 297:938-9; herein incorporated by reference). Many millions more suffer from venous stasis ulcers, lymphedema, peripheral vascular disease, non-healing surgical wounds, and burn wounds. It is estimated that between 5-10 billion dollars are spent annually in the US on wound care for chronic wounds (Kuehn (2007) *JAMA* 297:938-9; herein incorporated by reference).

By nature, all wounds contain some degree of bacteria. Wounds with increasing bacterial counts are said to be contaminated, then colonized, then critically colonized, and when the amount of bacteria exceeds $10^5$ per gram of tissue, the wound is said to be "infected" although it may or may not display the classic characteristics of infection such as frank pus, inflammation, and erythema. Although grossly infected wounds may represent a situation that requires more urgent intervention, it has been demonstrated that any amount of bacteria in a wound is detrimental to wound healing. Acute infections may occur in "fresh" acute wounds or in chronic wounds and may lead to tissue loss, limb loss, sepsis, or even death.

The effect of bacteria on wound healing is multifactorial, the sum of which is referred to as the bioburden. In general, the bacteria compete with the host for oxygen and nutrients, and create a pro-inflammatory environment that resists host defenses and places a metabolic strain on the wound. Normal growth factors and other pro-healing mechanisms may be hindered or even degraded by the bacteria, the end result of which is that wound healing is greatly prolonged. Over time, through adhesion to each other and the secretion of a proteinaceous matrix, the bacteria may form a biofilm which may be resistant to further treatment (Galiano et al (2007) in Grabb and Smith's Plastic Surgery, Lippincott Williams & Wilkins, Philadelphia, Pa.; herein incorporated by reference).

Since the early 1900s, the mainstay of wound treatment has been irrigation and mechanical debridement. This technique decreases bacterial counts and removes foreign bodies and necrotic tissue in which bacteria can proliferate, and thus aids wound healing, decreases the incidence of infection, and reduces the bioburden of the wound.

As adjuncts to mechanical debridement and irrigation, there are currently several different types of chemical debridement and antimicrobial agents that are used to decrease bacterial counts and remove necrotic tissue. However, the efficacy of these agents in removing biofilm and debriding necrotic tissue is minimal, as they do not penetrate the wound eschar and thus cannot reach the places where bacteria may reside.

Negative pressure wound therapy (NPWT) is a recent advancement in wound care. Among other beneficial actions, NPWT devices help remove bacteria and their secreted enzymes, thereby reducing bacterial counts and subsequently aiding wound healing. However, NPWT devices should not be used if necrotic tissue or active infection is present, and will not remove a biofilm or eschar. In addition, these devices are not meant to be used in areas under pressure (such as in a sacral pressure sore) and also require a cavity or indentation in the skin, which limits their use in superficial wounds.

Pulse lavage irrigation has been developed over the last 40 years and has been repeatedly shown to effectively decrease bacterial counts in wounds more efficiently and effectively than conventional methods of irrigation, including bulb syringe irrigation or gentle lavage, and is as effective at reducing bacterial counts as tangential hydrodissection (Granick et al (2007) *Ostomy Wound Manag.* 53:64-6, 68-70, 72; herein incorporated by reference). Pulse irrigation can be used in wounds of any depth or level of bacteria. At moderate pressures, pulse irrigation is non-injurious to viable tissue. In a small scale study using a caprine wound model and bioluminescent strain of *Pseudomonas aeruginosa*, pulse irrigation was shown to reduce bacterial counts more effectively than bulb irrigation (Svoboda et al (2006) *J Bone Joint Surg. Am.* 88:2167-74; herein incorporated by reference). Finally, pulse lavage has been shown to be more effective than whirlpool therapy in reducing bacterial counts (Krasner et al (2007) Chronic wound care: A clinical source book for healthcare professionals, 4th ed, Alvern, Pa., HMP Communications 331-342).

The major drawback to pulse lavage is that it is extremely messy and can easily contaminate the patient's surroundings, putting other patients and the person administering the treatment at risk. There have been case reports of pulse lavage irrigation spreading bacteria between patients (Maragakis et al (2004) *JAMA* 292:3006-11; herein incorporated by reference). Consequently, pulse lavage must be administered in a controlled environment. This limits the availability of pulse lavage as a therapeutic option and renders it unpracticable at the bedside, in home care and outpatient settings, and in military or field environments.

There is need in the art for improved methods of administering contained pulse lavage irrigation or contained pressurized non-pulsatile irrigation to aid wound healing.

SUMMARY OF THE INVENTION

The invention relates to the treatment of wounds. In particular, the invention relates to systems, devices, and methods enabling treatment (e.g., debridement) of wounds with liquid, gas, or particles in a non-controlled setting while providing containment of contaminated liquid, gas or particles, thereby preventing exposure of individuals and surfaces in proximity to the patient to infectious materials. In certain embodiments, the systems and devices are conformable to the contours of a non-planar surface, such as the human body (e.g., to seal or partially seal the device or system to a portion of a human body).

In some embodiments, the present invention provides systems and devices for wound irrigation comprising at least two, or all, of the following components: a) a wound-proximal membrane element; b) a base element, securable to the wound-proximal membrane element; c) a buffer component, wherein the buffer component is conformable to the contours of a non-planar surface, and wherein the buffer component is: i) securable to the wound-proximal membrane element, ii) securable to the base element, iii) is securable to the wound-proximal membrane element and the base element, or iv) forms part of the base element; d) an upper housing element, connectable to the base element, and bearing at least one port element; e) a fluid introduction means or component, connectable to the at least one port element; and f) a fluid suction means or component, connectable to the at least one port element.

In certain embodiments, the buffer component is composed of a material selected from the group consisting of: gel, foam, rubber, and sponge material. In other embodiments, the buffer component is inflatable. In certain embodiments, the buffer component comprises thin foil, pliable plastic, or silicon. In particular embodiments, the buffer component is constructed in an accordion-style fashion. In further embodiments, the buffer component is composed of a series of concentric shapes, wherein each shape in said series is larger than the preceding concentric shape.

In some embodiments, the invention comprises a wound-proximal membrane that provides a surface amenable to attachment of a base member of the device. In some embodiments, the wound-proximal membrane at least partially encompasses at least one wound site to which pulse irrigation lavage is to be directed. In some embodiments, the wound-proximal membrane protects the tissue surrounding the wound from maceration or damage during the pulse lavage irrigation procedure.

In some embodiments, the base member is affixed securely to the wound-proximal membrane. In some embodiments, dressing material at least partially encompasses the base member. In some embodiments, a housing element is securely and reversibly attached to the base member. In some embodiments, the attachment forms a watertight seal. In some embodiments, the housing element and the base element are combined into one element. In some embodiments, the housing element bears at least one dock serving as an introduction means for a port structure through which pulsed lavage irrigation fluid or pressurized non-pulsatile irrigation is introduced, or material is removed. In some embodiments, the port structure through which pulsed lavage irrigation fluid or pressurized non-pulsatile irrigation is introduced is a nozzle. In some embodiments, the port and dock form a watertight seal. In some embodiments, the at least one port and at least one dock comprise a structure permitting between 1° and 360° rotation of the nozzle. In some embodiments, the structure permitting between 1° and 360° rotation of said nozzle comprises a ball-in-cup design.

In some embodiments, the housing element bears at least one port through which irrigation fluid is removed. In some embodiments, the port interfaces with a dock. In some embodiments, the at least one port and dock form a watertight seal. In some embodiments, the removal of irrigation fluid occurs via mechanically-induced suction. In some embodiments, the removal of irrigation fluid occurs without mechanically-induced suction. In some embodiments, the force or rate of suction is adjustable so as to optimize the rate of irrigation fluid removal. In some embodiments, the port structure through which material is removed is a nozzle that may move vertically into and out of the wound, as well as rotate up to 360 degrees, thus permitting the nozzle to remove material directly from the wound surface. In various embodiments, the upper housing element, base element, and wound-proximal membrane are of dimensions capable of encompassing wounds of at least 0.5 cm; 0.5-1 cm; 1-5 cm; 5-10 cm; 10-20 cm; 20-50 cm; 50 cm-1 m; 1 m-1.5 m; 1.5-2 m; or 2-3 m. In various embodiments, the upper housing element, base element, and wound-proximal membrane are of dimensions capable of encompassing wounds of various shapes, including but not limited to circular wounds (e.g., puncture wounds, burns, abrasions, penetration wounds, gunshot wounds); linear wounds (e.g., cuts, slices, incisions, lacerations, blade-induced wounds); wounds with irregular shape (e.g., bedsores, ulcers, lacerations, tears, burns, abrasions).

In some embodiments, the housing element bears an additional at least one dock for optimal positioning of irrigation fluid introduction means and suction directionality. In some embodiments, unused docks are sealed with a plug. In some embodiments, the at least one plug and dock forms a watertight seal. In some embodiments, the structures comprising an irrigation fluid introduction means and irrigation fluid suction means comprise tubing. In some embodiments, there is a plurality of said tubing elements to permit multiple points of irrigation fluid introduction and/or irrigation fluid suction. In some embodiments, there is a connection means to bundle a plurality of irrigation fluid introduction or irrigation fluid suction tubing. In some embodiments, the connection means comprises a Y-tube connector. In some embodiments, the connection means comprises a multi-point connector. In some embodiments, the connections between tubing may be reversible, allowing optimal configuration of the tubing.

In some embodiments, the machine bears at least one place of attachment for at least one tubing, without limitation to the structural elements of this connection. In one embodiment, the connection between the tubing and machine may comprise a screw structure. In one embodiment, the connection between the tubing and machine may comprise a clasp structure. In one embodiment, the connection between the tubing and machine may comprise an interlocking structure. In one embodiment, the connection between the tubing and machine may comprise an interlocking collar-and-sleeve structure. In one embodiment, the connection between the tubing and machine may comprise a ball-and-socket structure. In some embodiments, the connection between the tubing and machine may form a watertight seal. In some embodiments, the connection between the tubing and machine may form an airtight seal. In some embodiments, the machine has irrigation pressure controls. The pressure at which the irrigation fluid is applied may be at least 5 psi; 5-7 psi; 7-10 psi; 10-15 psi; 15-20 psi; 20-25 psi; 25-30 psi; 30-40 psi; 40-50 psi; 50-75 psi; or 75-100 psi. In some embodiments, the pressure at which the irrigation fluid is applied is manually or automatically selected (e.g. based on selected criteria (e.g. wound depth, would type, wound size, patient age, patient size, etc.)). In some embodiments, the pressure at which the irrigation fluid is applied is selected from a range (e.g. 5-40 psi, 10-30 psi, 25-75 psi, 60-100 psi, 15-85 psi, etc.) within the range of 5-100 psi. In some embodiments, the machine has irrigation pulse frequency controls. The frequency at which the irrigation is pulsed may be at least 1 pulse per second (e.g.

1-2 pulses per second, 2-5 pulses per second, 5-10 pulses per second, 10-20 pulses per second, 20-50 pulses per second, 50-100 pulses per second, etc.). In some embodiments, the irrigation is pulsed at regular or non-regular intervals. In some embodiments, the machine has a setting that allows continuous non-pulsatile lavage. In some embodiments, the machine has a setting that allows control over the flow rate of irrigation fluid. In some embodiments, the flow rate at which the irrigation is applied is at least 0.05 liters per minute (e.g. 0.05-0.10 liters per minute, 0.10-0.25 liters per minute, 0.25-0.50 liters per minute, 0.50-1.0 liters per minute, 1-2 liters per minute, 2-5 liters per minute, 5-10 liters per minute). In some embodiments, optimal flow rate is manually or automatically adjusted. In some embodiments, the machine has a setting that allows control over the force of suction. In some embodiments, the suction pressure is at least 1 mm hg (e.g. 1-10 mm hg, 10-25 mm hg, 25-50 mm hg, 50-100 mm hg, 100-150 mm hg, 150-200 mm hg, 200-300 mm hg, 300-400 mm hg, 400-700 mm hg, 700-1000 mm hg, etc.). In some embodiments, the machine has a setting that allows the irrigation and suction to occur automatically. In some embodiments, the machine has a setting that allows the movement of the suction and irrigation ports to occur automatically. In some embodiments, the machine is powered by batteries. In some embodiments, the machine is powered by an external power source.

In some embodiments, the present invention provides a system for wound irrigation comprising (a) a wound-proximal membrane element, (b) a base element, securable to the wound-proximal membrane element, (c) an upper housing element, connectable to the base element, and bearing at least one port element, (d) a fluid introduction means, connectable to the at least one port element, and a fluid suction means, connectable to the at least one port element. In some embodiments, the fluid comprises irrigation fluid. In some embodiments, the at least one port element comprises at least two port elements. In some embodiments, the fluid introduction means is connected to one port element and the fluid suction means is connected to a second port element. In some embodiments, the system further comprises a means of adjusting of fluid pressure. In some embodiments, the system further comprises one or more irrigation nozzles for directing the flow of the fluid onto the wound. In some embodiments, the spray direction of one or more irrigation nozzles is manually controllable. In some embodiments, the spray direction of one or more irrigation nozzles moves according to a pre-set program. In some embodiments, the upper housing element connects to the base element by an interlocking mechanism. In some embodiments, the upper housing element connects to base element by a screw-in mechanism. In some embodiments, the base element securably attaches to the wound-proximal membrane element by an adhesive. In some embodiments, the base element securably attaches to the wound-proximal membrane element by a locking mechanism. In some embodiments, the wound-proximal membrane element adheres to a subject proximal to a wound on the subject.

In some embodiments, the present invention provides a method for administering an irrigation fluid to a wound comprising: (a) placing the system on the wound of a subject, (b) administering irrigation fluids to the wound, and (c) sequestering the irrigation fluids by the system following contact with the wound. In some embodiments, the irrigation fluid is administered via pulse lavage irrigation. In some embodiments, the irrigation fluid is administered via pressurized non-pulsatile irrigation.

In certain embodiments, the nozzle includes an internal or external structure to create laminar flow. In further embodiments, the nozzle is configured such that is has a round form on one aspect that allows it to sit in the housing structure and rotate. Alternatively the nozzle may not rotate and may be fixed in place.

In some embodiments, the present invention provides systems and devices for wound treatment (e.g., debridement) comprising: a) a base element, reversibly securable to a wound-proximal membrane element; b) an upper housing element, connectable to the base element, and bearing at least one port element, wherein the at least one port element may be or is connectable to a suction component; and c) a buffer component that is a separate component or forms part of the base element, wherein the buffer component is conformable to the contours of a non-planar surface, and wherein the buffer component is: i) reversibly or irreversibly securable to the wound-proximal membrane element, ii) reversibly or irreversibly securable to the base element, iii) is reversibly or irreversibly securable to the wound-proximal membrane element and the base element, and/or iv) is reversibly or irreversibly securable to the upper housing element.

In certain embodiments, the systems and devices further comprise the would proximal membrane element. In other embodiments, the at least one port element comprises first and second port elements, and wherein the first port element is connectable to the suction component, and the second port element is connectable to a material introduction component. In additional embodiments, the material introduction component is configured to introduce liquid, gas, or solid particles. In certain embodiments, the liquid comprises irrigation fluid. In additional embodiments, the material introduction component is connected to the first port element. In other embodiments, the systems and devices further comprise one or more nozzles for directing the flow of material onto the wound. In further embodiments, the housing element connects to the base element by an interlocking mechanism, by magnets, or by a screw-in mechanism. In additional embodiments, the base element securably attaches to the wound-proximal membrane element by an adhesive. In certain embodiments, the wound-proximal membrane element adheres to a subject proximal to a wound on the subject. In some embodiments, the buffer component is composed of a material selected from the group consisting of: gel, foam, rubber, PETG plastic, pliable plastic, thin foil, silicone, and sponge material.

In some embodiments, the present invention provides methods of treating (e.g., debridement) a wound comprising: a) placing a containment system on the outer surface of a subject such that at least part of a wound is enclosed and such that the containment system conforms to the outer surface of the subject creating a seal, wherein the containment system comprises a housing and at least one port component; and b) introducing and/or removing liquid, gas, or particles via the at least one port component such that at least partial treatment (e.g., debridement) of the wound is achieved without leakage of the liquid, the gas, and the particles outside of the containment system (e.g., leakage into the treatment environment).

In certain embodiments, the containment system further comprises a base element that is conformable to the outer surface of the subject. In other embodiments, the base element is flexibly attached to the housing. In additional embodiments, the base element is reversibly attached to the housing. In particular embodiments, the containment system further comprises a buffer component that is conformable to the outer surface of the subject. In additional embodiments, the buffer component is flexibly attached to the base element. In particular embodiments, the buffer component is reversibly attached to the base element. In further embodiments, the wound comprises a biofilm, and wherein the introducing and removing removes all or part of the biofilm.

In some embodiments, the seal is an airtight seal, liquid tight seal, and/or particle tight seal. In additional embodiments, the liquid is irrigation fluid which is administered via pulse lavage irrigation (e.g., and a wound with a biofilm is treated such that the biofilm is substantially removed). In certain embodiments, the liquid is irrigation fluid which is administered via pressurized non-pulsatile irrigation (e.g., and a wound with a biofilm is treated such that the biofilm is substantially removed). In additional embodiments, the introducing and/or removing liquid, gas, or particles comprises removing gas such that negative pressure is applied to the wound.

BRIEF DESCRIPTION OF THE DRAWINGS

FIG. 3 shows non-limiting exemplary embodiments for the base member connection to the wound-proximal membrane.

DEFINITIONS

As used herein, the term "wound" refers broadly to injuries to tissue including the skin, subcutaneous tissue, muscle, bone, and other structures initiated in different ways, for example, surgery, (e.g., open post cancer resection wounds, including but not limited to, removal of melanoma and breast cancer etc.), contained post operative surgical wounds, pressure sores (e.g., from extended bed rest) and wounds induced by trauma. As used herein, the term "wound" is used without limitation to the cause of the wound, be it a physical cause such as bodily positioning as in bed sores or impact as with trauma or a biological cause such as disease process, aging process, obstetric process, or any other manner of biological process. Wounds caused by pressure may also be classified into one of four grades depending on the depth of the wound: i) Grade I: wounds limited to the epidermis; ii) Grade II: wounds extending into the dermis; iii) Grade III: wounds extending into the subcutaneous tissue; and iv) Grade IV: wounds wherein bones are exposed (e.g., a bony pressure point such as the greater trochanter or the sacrum). The term "partial thickness wound" refers to wounds that are limited to the epidermis and dermis; a wound of any etiology may be partial thickness. The term "full thickness wound" is meant to include wounds that extends through the dermis.

As used herein, "wound site" refers broadly to the anatomical location of a wound, without limitation.

As used herein, the term "acute wound" refers to a wound that has not healed within 30 days.

As used herein, the term "chronic wound" refers to a wound that has not healed in a time period greater than 30 days.

As used herein, the term "subject" refers to both humans and animals, including, but not limited to, a dog, cat, bird, livestock, and preferably a human.

As used herein, the term "dressing" refers broadly to any material applied to a wound for protection, absorbance, drainage, treatment, etc. Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer) (Kannon and Garrett (1995) *Dermatol. Surg.* 21: 583-590; Davies (1983) *Burns* 10: 94; each herein incorporated by reference). The present invention also contemplates the use of dressings impregnated with pharmacological compounds (e.g., antibiotics, antiseptics, thrombin, analgesic compounds, etc). Cellular wound dressings include commercially available materials such as Apligraf®, Dermagraft®, Biobrane®, TransCyte®, Integra® Dermal Regeneration Template®, and OrCell®.

As used herein, "treatment environment" refers broadly to the surroundings of the individual receiving treatment, without limitation. These surroundings include but are not limited to a hospital, a clinic, a bedside, a residence, a battlefield, a trauma center, or a field environment.

As used herein, "adhesive" refers to any material with adherent properties used to affix one structure to another, including but not limited to the source of the substance (synthetic or natural) or the strength of the adhesion.

As used herein, "wound-proximal membrane" refers to a structure at least partially encompassing or covering at least one wound site without limitation to the nature of the material used for its construction and may or may not partially encompass some aspect of the "base", be that material synthetic or natural, and without limitation to its physical attributions including hardness, thickness, height, width, depth, shape, or transparency.

As used herein, "base" refers to a component of a device that is in contact with the subject, a wound-proximal membrane, or a buffer component; and the housing element. In one embodiment, the base element is separable from the housing element. In another embodiment, the base element is integrated with the housing element. In one embodiment, base element B (FIG. 1) has adhesive properties on its underside so that it adheres in a waterproof fashion to wound-proximal membrane C (FIG. 1) or to the patient directly, and has a waterproof locking mechanism that joins it to upper housing element A (FIG. 1), thereby permitting removal of the upper housing element, without limitation to the structural elements of this connection. In one embodiment, the connection between the base and upper housing element may comprise a screw structure. In one embodiment, the connection between the base and upper housing element may comprise a clasp structure. In one embodiment, the connection between the base and upper housing element may comprise an interlocking structure. In one embodiment, the connection between the base and upper housing element may comprise an interlocking collar-and-sleeve structure. In one embodiment, the connection between the base and upper housing element may comprise a ball-and-socket structure. In some embodiments, the connection between the base and upper housing element may form a watertight seal. The identity of the base element is not limited by the nature of the material used for its construction, be that material synthetic or natural, and without limitation to its physical attributions including hardness, thickness, pliability, height, width, depth, shape, diameter, or transparency.

As used herein, "housing" refers to a component of a device that completely or partially defines a chamber continuous with a wound site. The housing may or may not have one or more orifices that serve to allow connections between other structures of the device. The identity of the housing element is not limited by the nature of the material used for its construction, be that material synthetic or natural, and without limitation to its physical attributions including hardness, thickness, pliability, height, width, depth, shape, diameter, or transparency. In certain embodiments, the housing has a low profile (e.g., not a dome). In particular embodiments, the input/output ports and docks may be located on the sides of the of the structure.

As used herein, "dock" refers to an orifice in a housing element that serves as a means of connection between structures or elements of a device used for contained pulse lavage irrigation, or contained pressurized non-pulsatile irrigation or removal of material from the chamber continuous with the wound site, without limitation to the structural elements of this connection. In one embodiment, the connection between the dock and other structural elements may comprise a screw structure. In one embodiment, the connection between the dock and other structural elements may comprise a clasp structure. In one embodiment, the connection between the dock and other structural elements may comprise an interlocking structure. In one embodiment, the connection between the dock and other structural elements may comprise an interlocking collar-and-sleeve structure. In one embodiment, the connection between the dock and other structural elements may comprise a ball-and-socket structure. In some embodiments, the connection between the dock and other structural elements may form a watertight seal. The identity of a dock element is not limited by the nature of the material used for its construction, be that material synthetic or natural, and without limitation to its physical attributions including hardness, thickness, pliability, height, width, depth, shape, or transparency.

As used herein, "port" refers to a structural element that fits into the dock and may allow the introduction of pulse lavage irrigation, or pressurized non-pulsatile irrigation, into the housing chamber contiguous with the wound, or removal of material from the housing chamber, or serve another function related to the use of the device. In one embodiment, the port may comprise a nozzle that allows the introduction of pulse lavage irrigation, or pressurized non-pulsatile irrigation into the housing chamber contiguous with the wound. In one embodiment, the port may comprise a suction nozzle that allows removal of material from the housing chamber contiguous with the wound. In one embodiment, the port may comprise a plug that fits into a dock and serves to block the orifice of the dock in order to prevent the efflux of material from the housing chamber. In one embodiment, the plug may contain one or more perforations or hole to allow ventilation during the use of the device. The identity of a port is not limited by the nature of the material used for its construction, be that material synthetic or natural, and without limitation to its physical attributions including hardness, thickness, height, pliability, width, depth, shape, or transparency.

As used herein, "tubing" refers to a structure that provides a means by which to introduce material into the chamber continuous with the wound site, or remove material from the chamber continuous with the wound site. The identity of a tubing element is not limited by the nature of the material used for its construction, be that material synthetic or natural, and without limitation to its physical attributions including hardness, thickness, height, pliability, width, depth, shape, diameter, or transparency. In certain embodiments the tube (e.g., suction tube) may have a modification on the surface that enters the housing of the device. This may take the form of an enlargement or protrusion, a rough surface, without limitation to the structural elements of modification. The purpose of this is to allow the suction tube to gently scrape the surface of the wound in order to perform some element of mechanical debridement.

As used herein, "machine," when used in reference to a component of systems described herein, refers to a structure that propels the fluid into the tubing and into the chamber and may or may not provide a force that removes the fluid from the chamber. The identity of a machine is not limited by the nature of the material used for its construction, be that material synthetic or natural, and without limitation to its physical attributions including hardness, thickness, height, pliability, width, depth, shape, or transparency As used herein, "irrigation fluid" refers broadly to any material introduced into the chamber continuous with a wound site during the application of contained pulse lavage irrigation, or contained pressurized non-pulsatile irrigation. In one embodiment, the irrigation fluid is a gas. In a preferred embodiment, the irrigation fluid is a liquid. The irrigation fluid is not limited to any particular type or composition, including normal saline solution, buffer solution, antibiotic solution, bacteriostatic solution, antiseptic solution including Betadine® solution, surfactant solution, soap solution, or any combination thereof. In one embodiment, the irrigation fluid is normal saline. The irrigation fluid may include additional agents administered for therapeutic or analgesic properties including but not limited to thrombin, analgesic agents, growth factors, collagen-active agents, or a combination thereof. The irrigation fluid is not limited by the volume administered during each incidence of therapy which may comprise at least 0.01-0.1 L; 0.1-0.5 L; 0.5-1 L; 1-2 L; 2-3 L; 3-4 L; 4-5 L; 5-10 L; 10-20 L; 20-30 L; 30-40 L; 40-50 L; 50-100 L. The irrigation fluid is not limited by the nature of its physical attributes including but not limited to viscosity, color, transparency, temperature, pH, or density.

DETAILED DESCRIPTION OF THE INVENTION

The invention relates to the treatment of wounds. In particular, the invention relates to systems, devices, and methods enabling treatment (e.g., debridement) of wounds with liquid, gas, or particles in a non-controlled setting while providing containment of contaminated liquid, gas or particles, thereby preventing exposure of individuals and surfaces in proximity to the patient to infectious materials. In certain embodiments, the systems and devices are conformable to the contours of a non-planar surface, such as the human body (e.g., to seal or partially seal the device or system to a portion of a human body).

Figure 1:
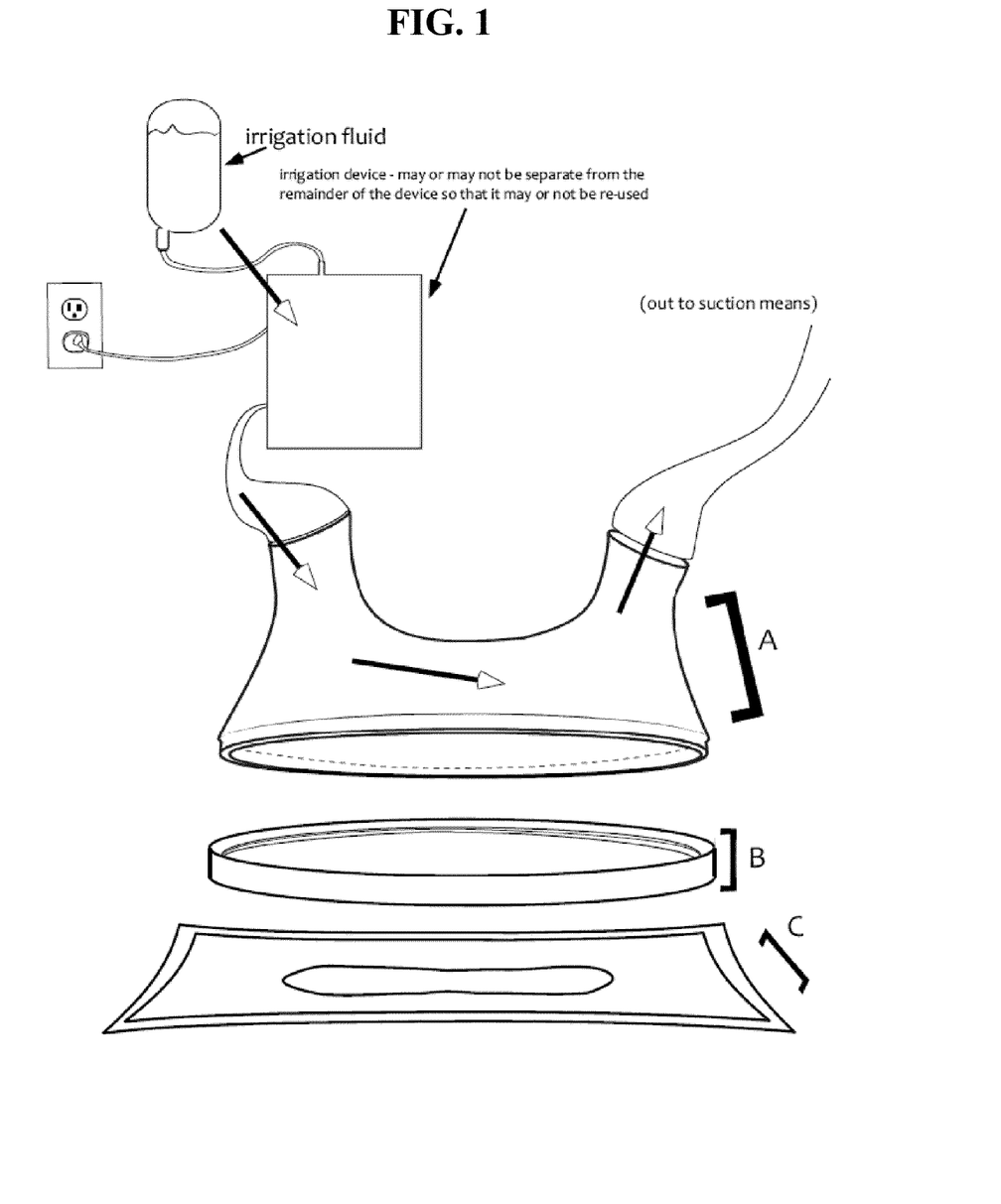
FIG. 1 shows an embodiment of a device. A, upper housing element; B, base element; C, wound-proximal membrane. Elements are shown in a separated state and are in an assembled state during wound irrigation therapy.

An embodiment of the invention as shown in FIG. 1 contains the following elements as described herein. In some embodiments, an irrigation device or system of the present invention comprises an upper housing, base element, and wound-proximal membrane. The system/device may also comprise an irrigation device, waste removal/storage device, pressure gauge, etc. It should be understood that this is an exemplary embodiment and that the invention is not limited to the specific features of this embodiment. In some embodiments, two or more of the elements of FIG. 1 are contained within a single element (e.g. upper housing element and base element, base element, and wound-proximal element, upper housing element, base element, and wound-proximal element). In some embodiments, the irrigation device is configured to engage and disengage the upper housing element. In some embodiments, the irrigation device and the upper housing element comprise a single unit. In some embodiments, the suction means is configured to engage and disengage the upper housing element. In some embodiments, the suction means and the upper housing element comprise a single unit.

Structural element C: A wound-proximal membrane. In some embodiments, the wound-proximal membrane comprises one or more membranes, sheets, films, and/or layers which contact the subject, wound, an/or area surrounding the wound to present a working field to the other portions of the device/system. The wound-proximal membrane may comprise different layers which are adhesive, fluid resistant, permeable, semi-permeable, impermeable, absorbent, breathable, and/or padded. In some embodiments, the specific make-up of the wound-proximal membrane is selected for the specific requirements of the subject, wound, and or irrigation procedure. In some embodiments, the wound-proximal membrane is permeable, semi-permeable, or impermeable to fluid (e.g. body fluids, irrigation fluids, water, etc.). In some embodiments, the wound-proximal membrane has a cut made in the center and a surrounding area of incomplete perforations or microperforations (such as is found in pieces of paper to facilitate "tearing along the dotted line") (SEE FIG. 4). The center cut may be of any suitable shape (e.g. an "x" shape, a circle, a line, etc.) and size. The perforations may be of any suitable conformation (e.g. ordered, random, linear, etc.) and/or number. In some embodiments, a wound-proximal membrane may comprise more than one center-cut. The cut is centered over the wound, and an area that contours to the wound edges is removed from the membrane, beginning from the pre-cut incision. An appropriate size and/or shape of wound-proximal membrane may be selected to appropriately suit a specific wound. If the wound is large and the base does not encircle the entire wound, the only area of the membrane that should be removed is the area within the perimeter of the base so that the irrigation and suction can take place unhindered. In some embodiments, only a portion of the wound is revealed to the irrigation fluid from beneath the wound-proximal membrane. The cut and the perforations facilitate tearing the membrane, or the membrane may be cut or trimmed to fit with scissors or other instrument. Alternatively, the center of the membrane may be trimmed/torn prior to placement on the patient if necessary. The purpose of the membrane is to protect the surrounding skin from maceration as well as to create a uniform surface upon which the base element may attach. This gives the base element a closer contour to the shape of the body, and helps seal the base element. The membrane may be a thin adhesive membrane, or may alternatively be composed of a thicker padding such as foam or soft rubber to help pad the wound edges and even the contour to achieve a better fit with the base element. The membrane may comprise any suitable material or materials (e.g. synthetic materials, natural materials, polymers, fibers, textiles, glass, plastic, metal, etc.). In some embodiments, the wound-proximal membrane is flat and engages the base element through suction or an adhesive. In some embodiments, the top side of the wound-proximal membrane comprises a rim element for engaging the base element (e.g. SEE FIG. 3). In some embodiments, a rim element and base element engage through an engagement mechanism (e.g. lip structure) (SEE FIG. 3B). In some embodiments, the rim element of the wound-proximal membrane enhances the seal between the base element and the wound-proximal membrane. In some embodiments, engagement between the base element and wound-proximal membrane is sufficient without a rim element. In some embodiments, negative pressure within the system/device enhances the interaction between the wound-proximal membrane and base element.

Structural element B: At least one base element is placed over the wound site. Alternatively, the at least one base element may be placed on the membrane before the housing element is placed on the wound. Alternatively, the base element is placed directly on or around the wound. The base element may adhere to the wound-proximal membrane via an adhesive surface on its underside. In some embodiments, the base element does not have to encircle the entire wound site, but should be located at least partially over the wound. In some embodiments, the base element surrounds the wound. Both the base element and the wound-proximal membrane are intended to remain on the wound site as long as the device is used, but may be replaced as necessary. The base element may have solely adhesive on its underside, or adhesive padding such as a soft rubber, silicone, or water-proof foam. The base element may be of any suitable shape (e.g. circular, ovular, square, rectangular, etc.) or size to best interact with the other elements of the device (e.g. upper housing and wound-proximal membrane) and properly engage the wound. In some embodiments, the inner diameter or perimeter of the base element is configured and sized for interaction with a upper housing element. In some embodiments, the outer diameter or perimeter of the base element is configured and sized for interaction with a upper housing element. In some embodiments, the inner diameter or perimeter of the base element is configured and sized for interaction with a wound-proximal membrane. In some embodiments, the outer diameter or perimeter of the base element is configured and sized for interaction with a wound-proximal membrane. The base element may be of any suitable shape and size. In some embodiments, the shape and size of the base element is selected based on case-specific criteria (e.g. wound size, wound shape, patient size, wound location, etc.).

Additional adhesive dressing or membrane may be placed around the perimeter lip of the base, to further seal it onto the wound-proximal membrane and to prevent the escape of irrigation fluid. This may also remain in place as needed. The additional dressing may have a pre-cut orifice that conforms to the outer perimeter lip of the base element, and should be attached after the base is placed on the other adhesive dressing.

Figure 6A:
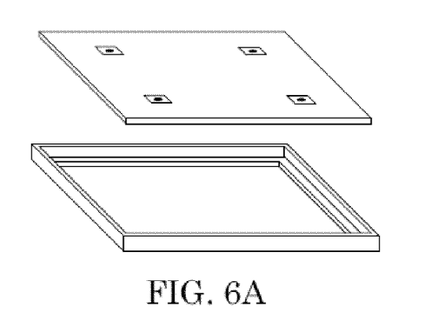
FIG. 6 shows several non-limiting exemplary embodiments of the base member element and upper housing element, and connection thereof, including a rectangle shape (6A), circle shape (6B), a rectangle shape with pyramid shape for upper housing element (6C), and circle shape with center raised portion (6D).
Figure 6B:
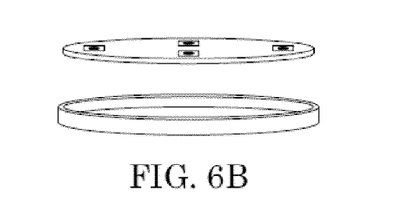
Figure 6C:
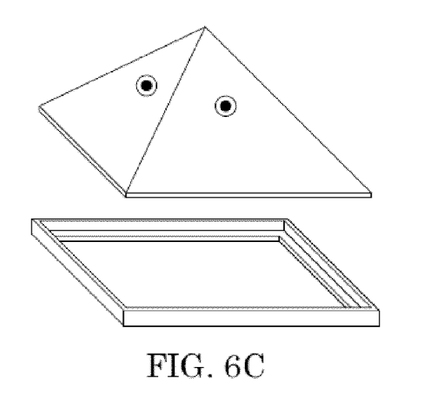
Figure 6D:
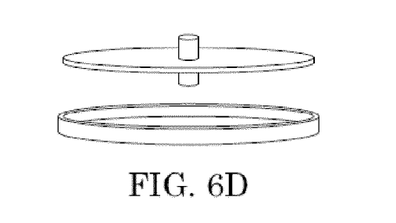

Structural element A: The upper housing element. In some embodiments, the upper housing element is temporarily secured to the base element to form a watertight junction. In some embodiments, the upper housing element provides entry and exit points (e.g. ports, valves, etc.) for irrigation fluid (SEE FIG. 1). In some embodiments, the upper-housing element may be of any suitable shape (e.g. dome (SEE FIG. 2), flat (SEE FIG. 6A/B, pyramidal (SEE FIG. 6C), etc.) and size. In some embodiments, the shape and size of the upper housing is selected based on case-specific criteria (e.g. wound size, wound shape, patient size, wound location, etc.). In some embodiments, the shapes and sizes of the upper housing element, base element, and wound-proximal membrane are selected to complement each other and function in conjunction (SEE FIGS. 1, 2, 3, and 6).

Figures 2, 2A:
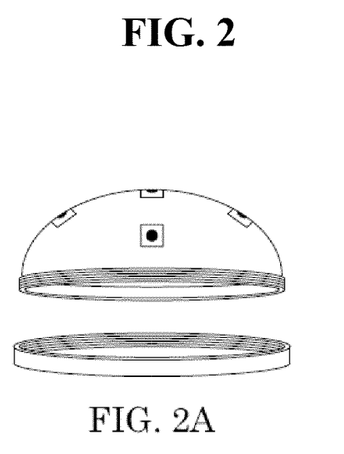
FIG. 2 shows several non-limiting exemplary embodiments for the upper housing element connection to the base element via a screw structure (e.g. threading); B, interlocking structure (e.g. lock-in place); C, notched-fit.
Figure 2B:
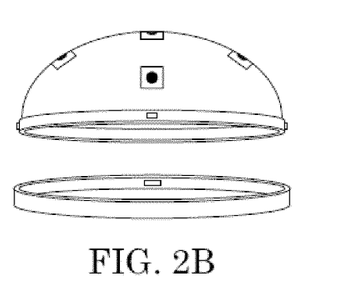
Figure 2C:
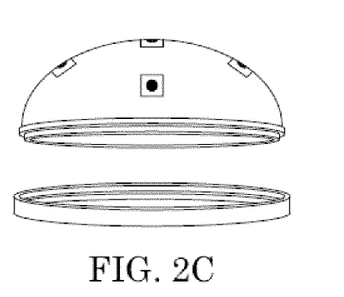
Figure 3A:
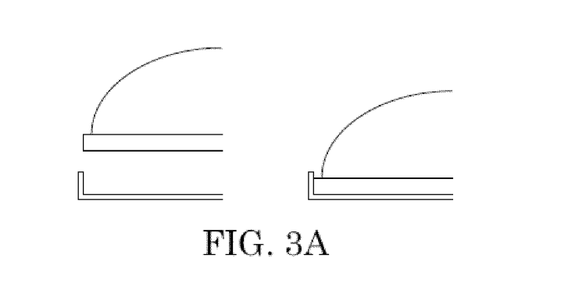
FIG. 3A shows the wound-proximal membrane without an over-lying ridge and FIG. 3B shows the wound-proximal membrane with an over-lying ridge for further securing to the base member.
Figure 3B:
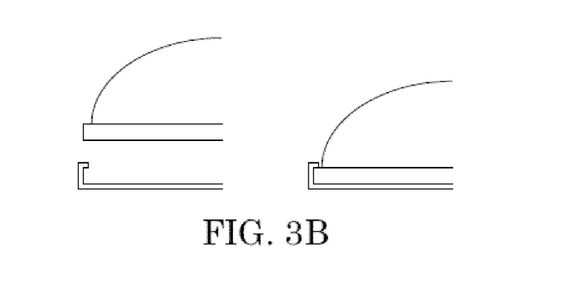
Figure 4A:
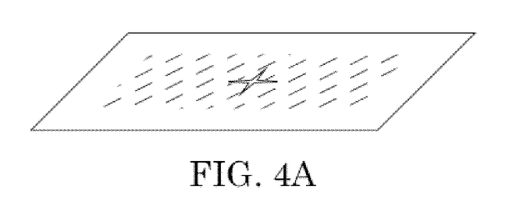
FIG. 4 shows an embodiment of the wound-proximal membrane component from both an perspective view (4A) and a top-down view (4B).
Figure 4B:
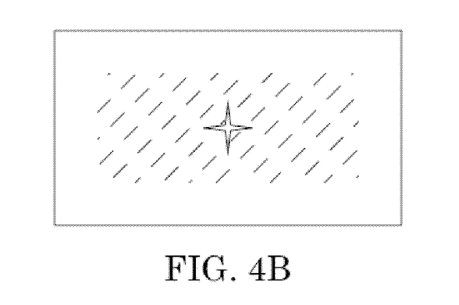

Different embodiments for the junctions between the upper housing, base element, and wound-proximal membrane are exemplified in FIG. 2 and FIG. 3. Examples of the upper housing and base element junction include screw (SEE FIG. 2A), snap, fit (SEE FIG. 2C), lock, or clasp mechanisms (SEE FIG. 2B), or other means that provide for a watertight junction (e.g. temporary watertight junction). The inferior bottom of the upper housing element may rest within the inner perimeter of the base, with the lateral bottom of the upper housing element resting on top of the base. The upper housing element may be removed from the base element between uses to allow the wound to be dressed in any manner desired. In some embodiments, the junction between the upper housing and the base element is configured for routine and repeated engagement and disengagement. In some embodiments, the upper housing comprises 1 or more docks or ports (e.g. 1, 2, 3, 4, 5, 6, 7, 8, 9, 10 . . . 20, etc.) for engagement of other device elements including, but not limited to means for providing irrigation fluid, suction means, etc. In some embodiments, docks and/or ports are generically configured for attachment to any additional device elements. In some embodiments, ports and/or docks are configured for attachment to a specific element (e.g. irrigation means, suction means, pressure monitoring means, etc.).

Figure 5A:
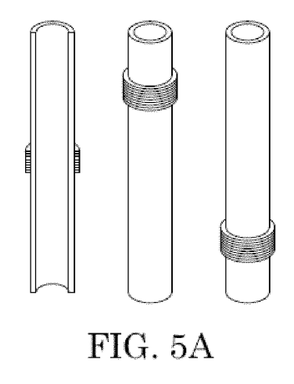
FIG. 5 shows non-limiting exemplary embodiments of: A, suction port(s); B/C, irrigation nozzle element(s); and D, plug elements.
Figure 5B:
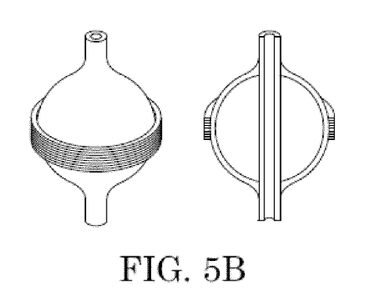
Figure 5C:
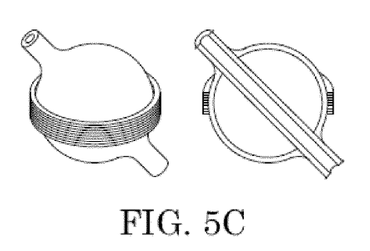
Figure 5D:
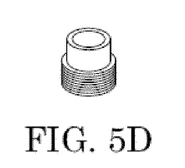

Additional structural elements, as described herein:

The suction tubing (SEE FIG. 5A), irrigation nozzle(s) (SEE FIG. 5B/C), and plug(s) (SEE FIG. 5D) may be attached to the upper housing element either before or after it is secured to the base element. When a plurality of docks is present, these accessories can be interchangeably and reversibly placed within the various docks in order to optimize suction and irrigation. In a preferred embodiment, the seal between the docks and accessories is watertight and/or airtight.

The suction and irrigation tubing is secured at one end to the irrigation nozzles and suction nozzles, and at the other end to the machine(s). The tubing may be separated from the upper housing element and the machine(s) between uses to prevent contamination. The connection between the nozzle or other irrigation fluid introduction structure and the tubing as well as the connection between the machine(s) and the tubing is secure enough to withstand movement but also easily released. If more than one suction tube or irrigation nozzle is to be used on the upper housing element, Y tubing or a multi-point connection can be used to attach multiple nozzles or suction tubes to the upper housing element. In some embodiments, suction and/or irrigation tubing contains one or more valves, ports, splitters, etc. In some embodiments, suction and/or irrigation tubing is attached to the upper housing elements at one or more ports and/or docks (e.g. 1, 2, 3, 4, 5, 6, 7, 8, 9, 10 . . . 20, etc.). In some embodiments, the present device comprising tubing of any suitable configuration required for the specific irrigation task. After connecting the machine to a supply of irrigation fluid, the machine is turned on, and the irrigation is controlled by aiming the flow via manual manipulation of irrigation nozzle(s). In an alternative embodiment, the movement of the irrigation nozzles and suction nozzles is automated. The irrigation nozzle(s) has 360° rotational movement within the upper housing element. In one embodiment, this freedom of movement is provided by a "ball in cup" design. This freedom of movement allows targeted pulse irrigation for optimized removal of biofilm. In one embodiment, fluid is removed by manipulating the suction ports, which have free vertical movement and at least some horizontal movement. In some embodiments, the machine which supplies irrigation fluid comprises a single unit with the upper housing element. In some embodiments, the machine to a supply of irrigation fluid engages the upper housing element at an irrigation hose or tube, dock, port, and/or inlet valve.

After sufficient irrigation, the upper housing element and tubing are removed, and the wound covered and dressed per routine. In some embodiments, the pulse irrigation and/or suction machines are re-usable and when properly used do not result in cross-contamination between patients. In an alternative embodiment, the machine is disposable. In some embodiments, the wound-proximal membrane, dressing, and all other components of the device are disposable and are discarded after the patient has completed therapy. In one embodiment, the disposable components are packaged together and the machine(s) are packaged separately.

Wound-proximal membrane, base element(s), and upper housing element(s) are available in a variety of sizes and shapes (e.g. circular, ovular, square, rectangular, etc.) to allow optimal irrigation on different wound sites regardless of anatomical position or size of the wound. In some embodiments, a kit is provided containing a plurality of components of different sizes and shapes that can be mixed and matched as needed.

In some embodiments, the upper housing element, base element, and wound-proximal membrane are of dimensions capable of encompassing wounds of a variety of diameters. In some embodiments, the upper housing element, base element, and wound-proximal membrane are of dimensions capable of encompassing wounds of a variety of shapes.

In some embodiments, the upper housing element and base element are constructed to permit the application of negative pressure to the wound. In some embodiments, absorbent material (e.g., sponge, etc.) is included within the wound-proximal chamber. In some embodiments, negative pressure is applied to the wound by the application of suction. In further embodiments, excess fluid or wound-produced fluid is removed through a nozzle that may move vertically into and out of the wound, thus permitting the nozzle to remove material directly from the wound surface.

In certain embodiments, the systems and devices are conformable to the contours of a non-planar surface, such as the human body (e.g., to seal or partially seal the device or system to a portion of a human body). In some embodiments, a buffer component is employed to allow the devices of the present invention to seal or partially seal with a portion of a body that has a wound. In particular embodiments, the buffer component is differentially compressible so that on one of its surfaces, the seal over the contours of the body is maintained and the buffer component is still capable of attaching to the less flexible dome.

In buffer component can broadly be described as a component that may be a separate or integrated piece of the device that adapts the device to the curved surfaces of the body. The buffer component may enclose the entire wound, may enclose part of the wound, or may rest on top of or within the wound, without limitation to the structural elements of the connection between the buffer and the body. The buffer component may attach directly to the wound, or may rest on top of an adhesive dressing, which attaches to the wound. On one surface, the buffer component may adhere to the body via an adhesive. On one surface, the buffer component may adhere to the body via a separate or integrated suction mechanism. On one surface, the buffer component may adhere to the body via straps or belts or other fasteners. On the other surface, the buffer component may adhere to the other components of the device without limitation to the structural elements of the connection. This connection may be reversible or irreversible. On the other surface, the buffer component may attach to the other components of the device, for example, via an adhesive, via an interlocking mechanism, via a screw mechanism, via a ball and socket mechanism, via a half turn mechanism, etc. In some embodiments, the buffer component is intended to remain on the patient between uses. In another embodiment, the buffer component is intended to be removed between uses. The shape of the buffer component may be the same or different size or shape than the base. The buffer component may be of uniform or non-uniform size and shape, and may have a differential shape so that it serves as a connector or adaptor between a base and a housing that are of different shapes.

Figure 7:
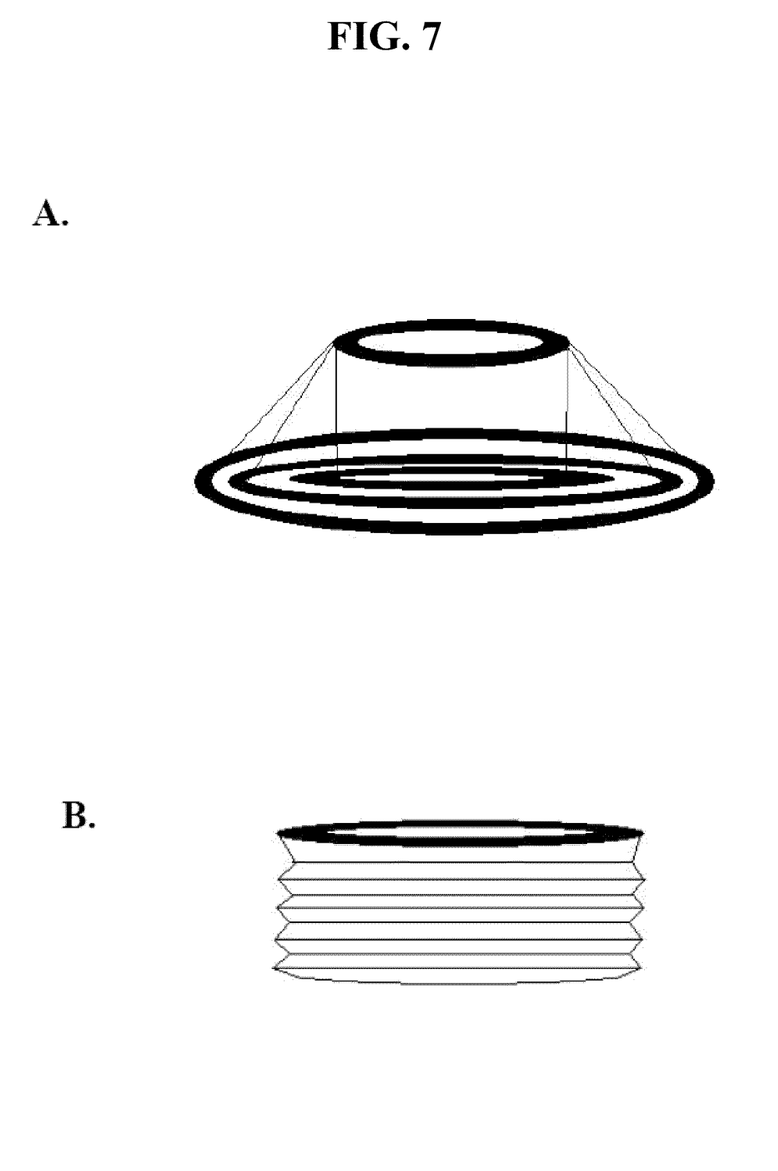
FIG. 7A shows one embodiment of forming the buffer component from a series of concentric circles.
FIG. 7B shows one embodiment showing an according-style for the buffer component.
Figure 8A:
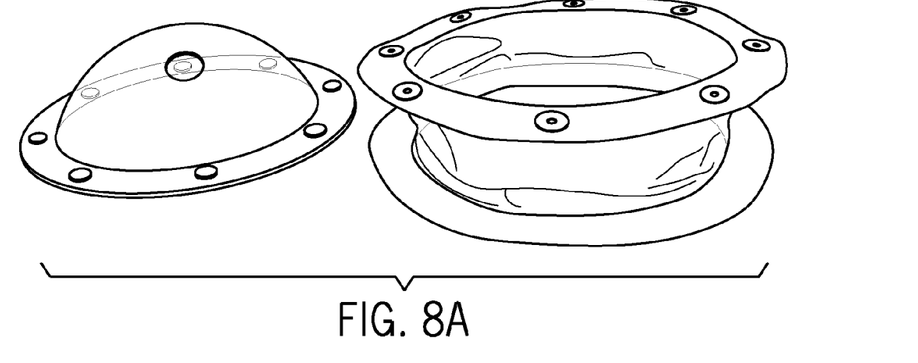
FIG. 8A shows a side view of an upper housing element (left side) and base component with integrated buffer component (right side).
Figure 8B:
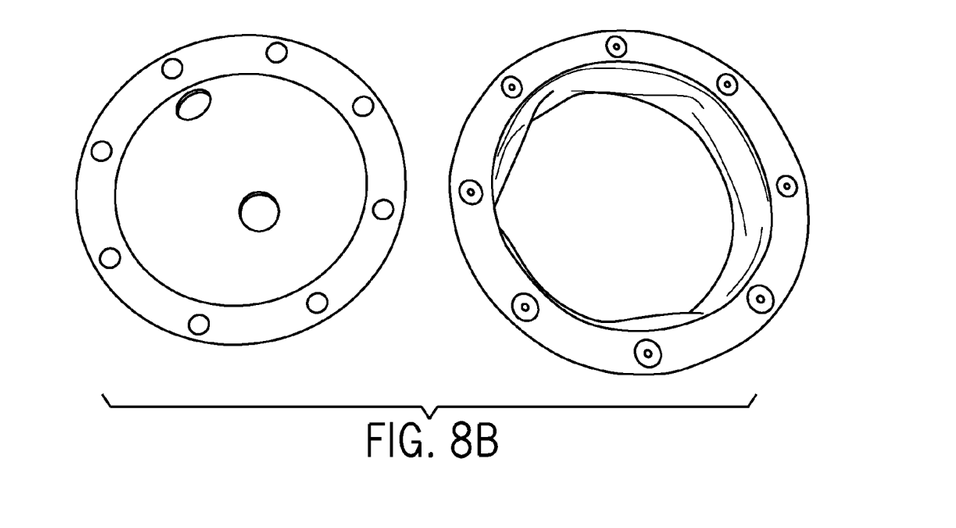
FIG. 8B shows a top down view of an upper housing element (left side) and base component with integrated buffer component (right side).
Figure 8C:
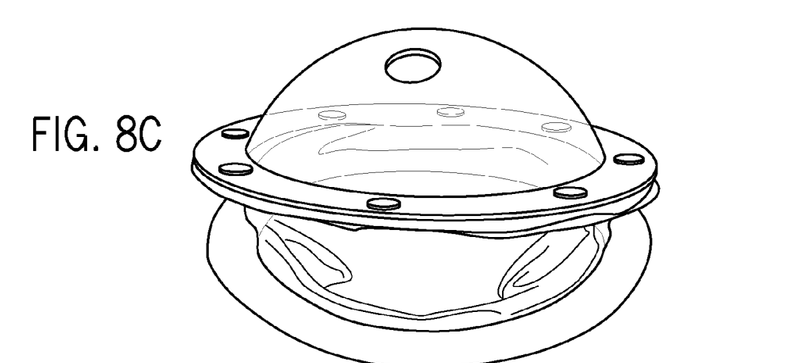
FIG. 8C shows a side view of an upper housing element reversibly attached to a base component via magnets on the two components.

In certain embodiments, the buffer component is composed of a series of concentric shapes (e.g., that rest on or around the wound). In one embodiment, these comprise a series of concentric rings, with the same or different thickness, and the same or different width, with increasing diameter. Each shape in this series is larger than the shape preceding it. These shapes may all be connected to another structure via a flexible and pliable material such as a thin plastic sheet or foil. The structure that is connected to the concentric shapes may be comprised of a ring or other shape, and is designed to attach to the dome or housing piece of the main device without limitation to the structural elements of the connection. This connection may be reversible or irreversible. This attachment may be comprised of an adhesive, an interlocking mechanism, a screw mechanism, a ball and socket mechanism, a half turn mechanism, or any other temporary or permanent mechanism, and may form an air and water tight seal. Each of the concentric shapes individually connects to the same or different other structure. The material used for the connection may have an incomplete perforation that extends around the perimeter of the material, either near the concentric shapes or near the other structure to facilitate tearing. This is designed so that the concentric shape of the proper size can be placed around or over the wound and the other shapes can be removed, while maintaining the connection to the other structure which will connect to the housing part of the device. One embodiment of forming the buffer component from a series of concentric circles is shown in FIG. 7A.

In another embodiment, the buffer component is composed of a material that is constructed in an accordion-style fashion, whereby the material is folded or compressed in such a fashion that it different parts of it may be decompressed or unfolded while other parts remain compressed or folded. In this embodiment, the buffer component may be composed of, for example, plastic, metal, foil, silicone, without limitation to the type of material used in this composition. In this embodiment, the buffer component may adhere to the patient surface beneath the base of the main device, above the base of the device and below the connection to the base, or above the connection to the base and below the dome. One embodiment showing an according-style for the buffer component is shown in FIG. 7B.

In another embodiment, the buffer component is composed of a flexible material that may or may not add any structural support to the device such as a thin foil or a thin piece of plastic (e.g., similar to a plastic bag). In this embodiment, the buffer component serves as an attachment between two components of the device, or between the patient and one component of the device, and by virtue of the fact that the buffer component does not lend structural support, it allows relative movement between elements of the device. In this embodiment, the buffer component may adhere to the patient surface beneath the base of the device, above the base of the device and below the connection to the base, or above the connection to the base and below the dome.

In another embodiment, the buffer component is composed of a material that is differentially compressible so that when pressure is applied, different areas of the buffer component may have different heights and when pressure is released, the buffer component may or may not return to its original configuration. In this embodiment, the buffer component may be composed of, for example, a gel, a foam, a rubber, a sponge, or any other differentially compressible material that allows part of the buffer component to be compressed while other part(s) are variably compressed. In this embodiment, the buffer component may adhere to the patient surface beneath the base of the device, above the base of the device and below the connection to the base, or above the connection to the base and below the dome.

In another embodiment, the buffer component is composed of an inflatable structure into which a gas or fluid can be injected. In this embodiment, inflation of the structure with either gas or fluid will allow the buffer to be differentially compressible, and maintain its attachments to the patient and to the remainder of the system. In this embodiment, the buffer may adhere to the patient surface beneath the base of the device, above the base of the device and below the connection to the base, or above the connection to the base and below the dome.

In some embodiments, a system is provided comprising one or more of the above components as well as, optionally, instructions for use, computer equipment and software, or other components for using, monitoring, or automating one more or more components of the system.

I claim:

1. A system for wound treatment comprising:
a) a base element comprising a top and bottom, wherein the bottom is:
   i) conformable to contours of a non-planar surface, and
   ii) securable to a surface of a body or to a wound-proximal membrane element residing upon the surface of a body;
b) an upper housing element, connectable to the top of said base element, less flexible than said base element and comprising at least first and second port elements;
c) a material introduction component, connected to said first port element, and one or more nozzles for directing the flow of the material onto said surface of a body or said wound-proximal membrane element residing upon the surface of a body; and
d) a fluid suction component, connected to said second port element;
wherein the base element is differentially compressible so that the bottom is conformable to contours of a non-planar surface while the top is attached to the less flexible upper housing element.

2. The system of claim 1, further comprising said wound proximal membrane element.

3. The system of claim 1, wherein said upper housing element connects to said base element by an interlocking mechanism, by magnets, or by a screw-in mechanism.

4. The system of claim 1, wherein said base element securably attaches to said wound-proximal membrane element by an adhesive.

5. A method of treating a wound comprising:
   a) placing a containment system of claim 1 on an outer surface of a subject such that at least part of a wound is enclosed within said containment system and such that said containment system conforms to said outer surface of said subject creating a seal; and
   b) introducing liquid, gas, or particles with said material introduction component via said first port element and said one or more nozzles; and
   c) removing said liquid, gas, or particles with fluid suction component via said second port element,
such that at least partial treatment of said wound is achieved without leakage of said liquid, said gas, and said particles outside of said containment system.

6. The method of claim 5, wherein an airtight seal, liquid tight seal, and/or particle tight seal is formed between said containment system and said outer surface of a subject.

7. The method of claim 5, wherein said liquid is irrigation fluid which is administered via pulse lavage irrigation or pressurized non-pulsatile irrigation.

8. A system for wound irrigation comprising:
   a) a base element that is:
      i) conformable to contours of a non-planar surface, and
      ii) securable to a surface of a body or to a wound-proximal membrane element residing upon the surface of a body;
   b) an upper housing element comprising at least first and second port elements, wherein the upper housing is less flexible than the base element;
   c) a buffer component, wherein the buffer component has a top and a bottom, wherein the bottom is connectable to the base element and the top is connectable to the upper housing, wherein the buffer component is differentially compressible so that the bottom is conformable to contours of a non-planar surface while the top is attached to the less flexible upper housing element;
   d) a material introduction component, connected to said first port element, and one or more nozzles for directing the flow of the material onto said surface of a body or said wound-proximal membrane element residing upon the surface of a body; and
   e) a fluid suction component, connected to said second port element.

9. The system of claim 8, further comprising said wound proximal membrane element.

10. The system of claim 8, wherein said buffer component is composed of a material selected from the group consisting of: gel, foam, rubber, PETG plastic, pliable plastic, thin foil, silicone, and sponge material.

11. A method of treating a wound comprising:
   a) placing a containment system of claim 8 on an outer surface of a subject such that at least part of a wound is enclosed by said containment system and such that said containment system conforms to said outer surface of said subject creating a seal; and
   b) introducing liquid, gas, or particles with said material introduction component via said first port component and said one or more nozzles; and
   c) removing said liquid, gas, or particles with fluid suction component via said second port element,
such that at least partial treatment of said wound is achieved without leakage of said liquid, said gas, and said particles outside of said containment system.

12. The method of claim 11, wherein said liquid is irrigation fluid which is administered via pulse lavage irrigation or pressurized non-pulsatile irrigation.

13. A system for wound treatment comprising:
   a) a base element comprising a top and bottom, wherein the bottom is:
      i) conformable to contours of a non-planar surface, and
      ii) securable to a surface of a body or to a wound-proximal membrane element residing upon the surface of a body;
   b) an upper housing element, connectable to the top of said base element by an interlocking mechanism, by magnets, or by a screw-in mechanism, wherein said upper housing element is less flexible than said base element and comprises at least first and second port elements;
   c) a material introduction component, connected to said first port element; and
   d) a fluid suction component, connected to said second port element;
wherein the base element is differentially compressible so that the bottom is conformable to contours of a non-planar surface while the top is attached to the less flexible upper housing element.

14. The system of claim 13, further comprising said wound proximal membrane element.

15. The system of claim 13, wherein said base element securably attaches to said wound-proximal membrane element by an adhesive.

16. A system for wound irrigation comprising:
   a) a base element that is:
      i) conformable to contours of a non-planar surface, and
      ii) securable to a surface of a body or to a wound-proximal membrane element residing upon the surface of a body;
   b) an upper housing element comprising at least first and second port elements, wherein the upper housing is less flexible than the base element;
   c) a buffer component, wherein the buffer component has a top and a bottom, wherein the bottom is connectable to the base element and the top is connectable to the upper housing by interlocking mechanisms, by magnets, and/or by screw-in mechanisms, wherein the buffer component is differentially compressible so that the bottom is conformable to contours of a non-planar surface while the top is attached to the less flexible upper housing element;
   d) a material introduction component, connected to said first port element; and
   e) a fluid suction component, connected to said second port element.

17. The system of claim 16, further comprising said wound proximal membrane element.

18. The system of claim 17, wherein said base element securably attaches to said wound-proximal membrane element by an adhesive.

19. The system of claim 16, wherein said buffer component is composed of a material selected from the group consisting of: gel, foam, rubber, PETG plastic, pliable plastic, thin foil, silicone, and sponge material.

* * * * *